United States Patent [19]

Casarcia

[11] Patent Number: 4,644,274
[45] Date of Patent: Feb. 17, 1987

[54] APPARATUS FOR SUPPORTING AN EDDY CURRENT PROBE USED TO SCAN AN IRREGULAR SURFACE

[75] Inventor: Dominick A. Casarcia, Cincinnati, Ohio

[73] Assignee: General Electric Company, Cincinnati, Ohio

[21] Appl. No.: 481,138

[22] Filed: Apr. 1, 1983

[51] Int. Cl.⁴ .................. G01N 27/90; F16H 29/00
[52] U.S. Cl. .................................. 324/262; 324/237; 324/226; 324/225; 324/239; 74/89.21
[58] Field of Search ............... 324/262, 226, 217, 260, 324/261, 225, 226, 228, 234, 238, 237, 240, 173, 174; 74/89.2, 89.21, 89.22

[56] References Cited

U.S. PATENT DOCUMENTS

| | | | |
|---|---|---|---|
| 3,793,545 | 2/1974 | Leiber et al. | 324/174 X |
| 3,919,628 | 11/1975 | Mandula et al. | 324/261 |
| 3,926,053 | 12/1975 | Schurver et al. | 324/207 X |
| 3,936,723 | 2/1976 | Clary | 324/262 |
| 4,066,949 | 1/1978 | Condrac | 324/207 X |
| 4,219,774 | 8/1980 | Rogel et al. | 324/262 |
| 4,258,319 | 3/1981 | Shimada et al. | 324/226 |
| 4,270,089 | 5/1981 | Häberlein | 324/262 |
| 4,274,054 | 6/1981 | Savidge et al. | 324/225 |
| 4,409,549 | 10/1983 | Garner et al. | 324/262 |
| 4,430,614 | 2/1984 | Gereg | 324/262 X |
| 4,434,659 | 3/1984 | Kurtz et al. | 324/262 X |
| 4,445,089 | 4/1984 | Harrison | 324/262 X |
| 4,468,620 | 8/1984 | Vaerman | 324/262 X |

FOREIGN PATENT DOCUMENTS 1318346  5/1973  United Kingdom ............... 324/237

Primary Examiner—Reinhard J. Eisenzopf
Assistant Examiner—Warren S. Edmonds
Attorney, Agent, or Firm—Gregory A. Welte; Derek P. Lawrence

[57] ABSTRACT

An invention is disclosed which supports an eddy current probe at a predetermined distance from a surface to be scanned. In another embodiment, the probe is scanned by rotation about an axis and along an arc of predetermined length and position.

2 Claims, 8 Drawing Figures

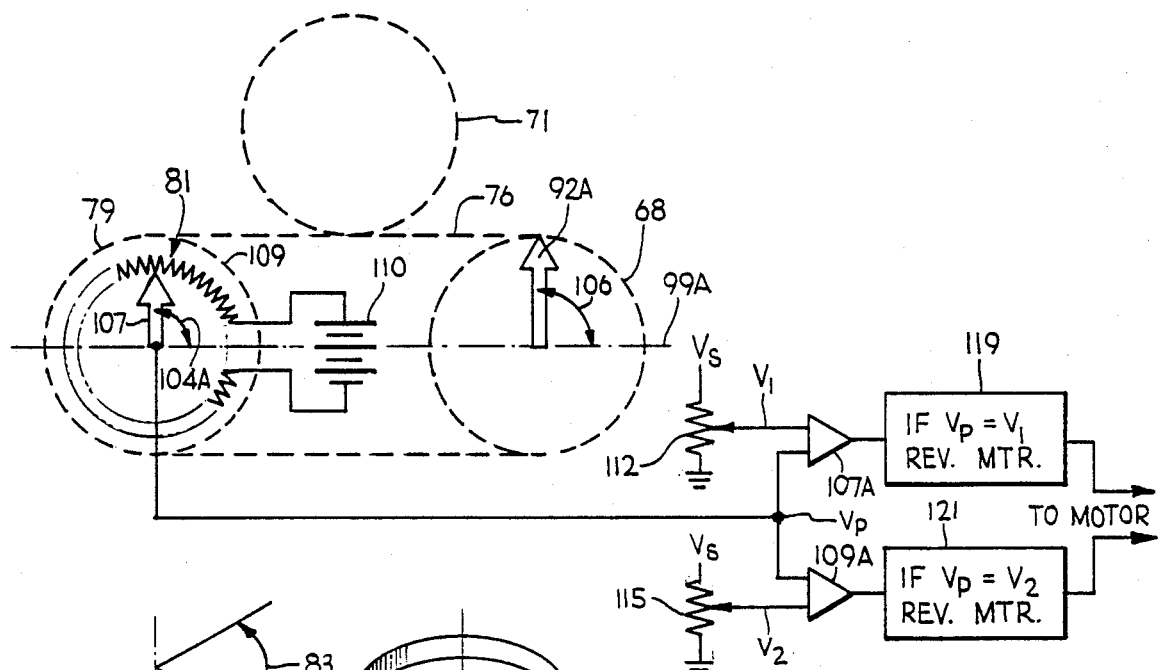
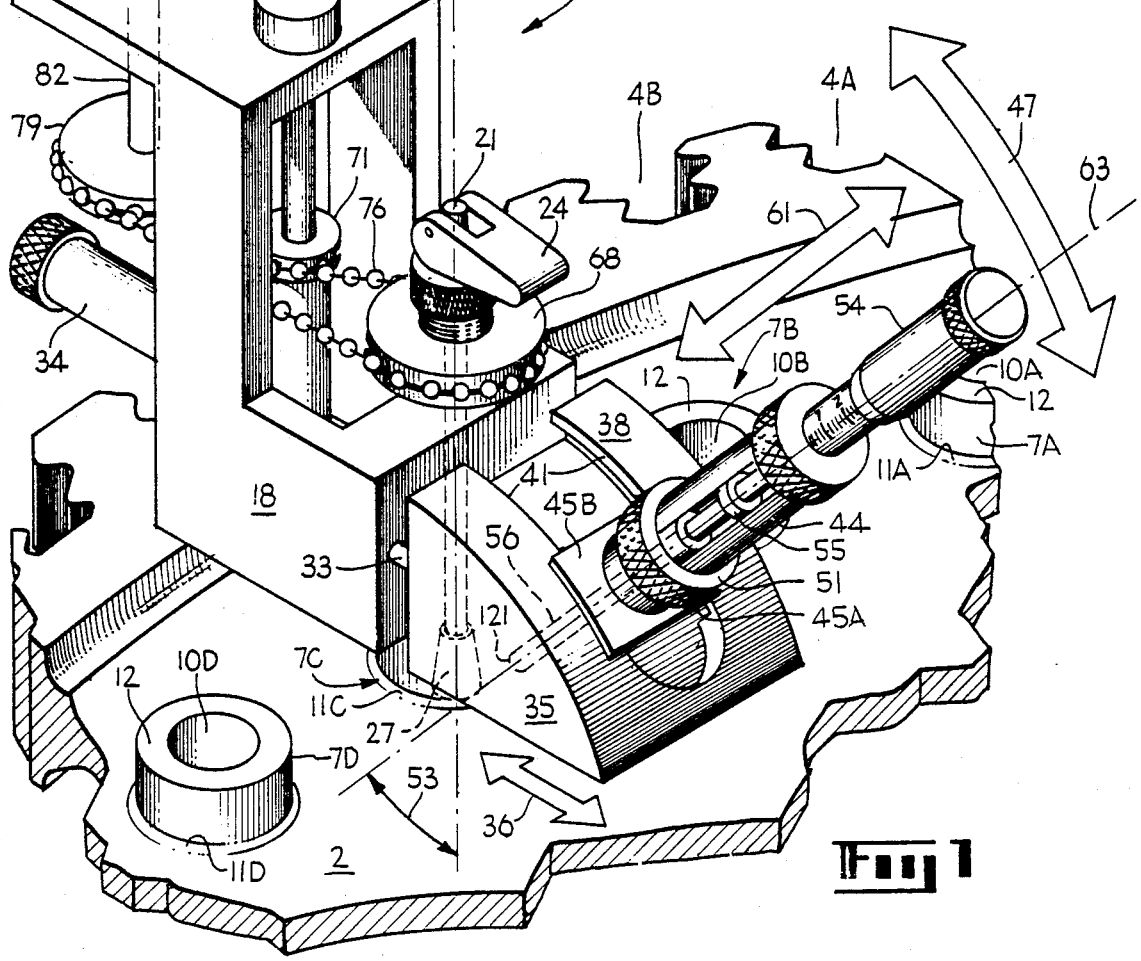

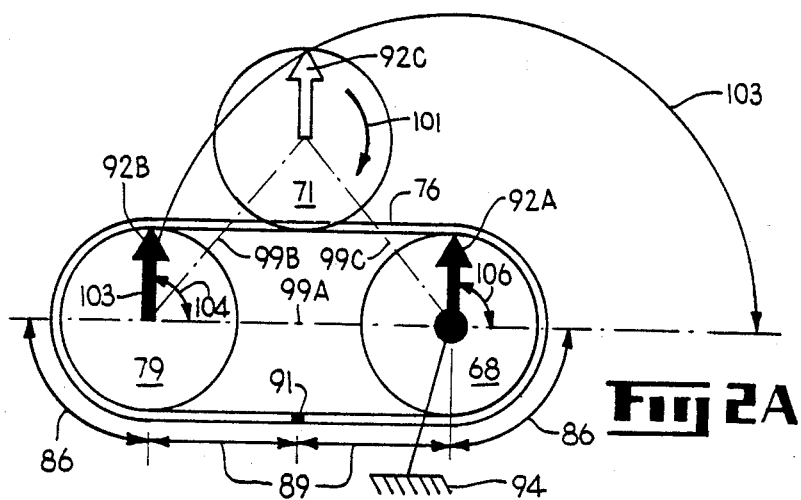
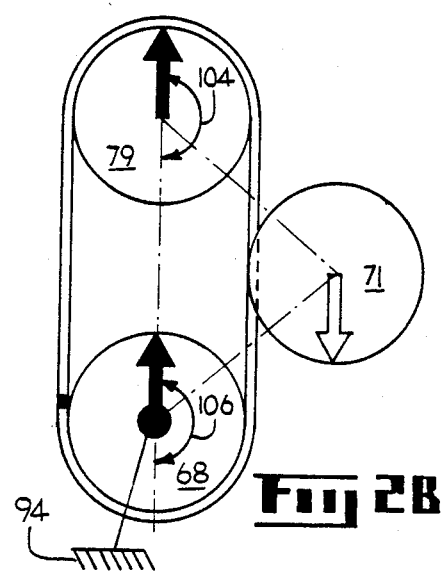
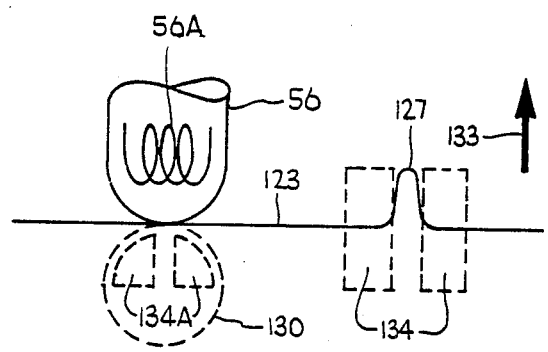
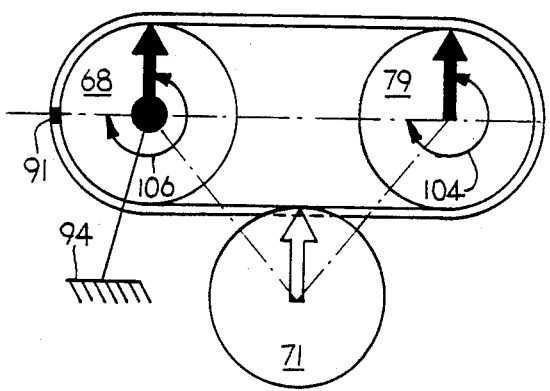
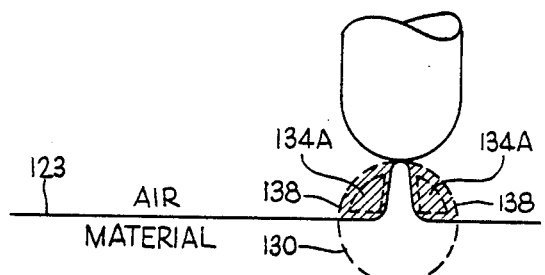
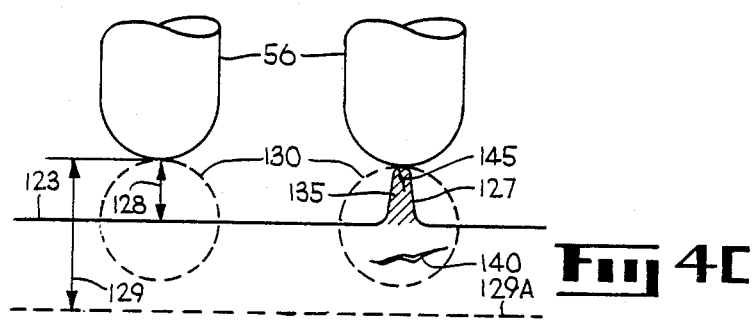

APPARATUS FOR SUPPORTING AN EDDY CURRENT PROBE USED TO SCAN AN IRREGULAR SURFACE

The present invention relates to a bracket which supports an eddy current probe, and, more particularly, to such a bracket which supports a probe at a fixed distance from a surface to be scanned.

BACKGROUND OF THE INVENTION

Eddy current probes are used to scan the surface of a material to locate flaws. A problem arises in distinguishing flaws from mere irregularities in the shape of the surface. For example, an irregularity may appear as a small bump which results from the grinding of a welding bead of a seam, yet may not be considered a flaw. However, the bump tends to mask eddy current signals produced by flaws near it.

Further, if the eddy current probe is scanned along the surface up to the bump and then either accidentally bounced away from the surface because of impact with the bump or intentionally raised to hurdle the bump, the bouncing and raising themselves produce lift-off signals which tend to mask the signals produced by the flaws.

Similarly, lift-off signals occur when scanning is undertaken of a fillet on a boss of a gas turbine engine rotor when the eddy current probe reaches a surface irregularity caused by, not a welding bead, but a bump left by the parting line of a mold used to shape the boss in an electrochemical machining process.

OBJECTS OF THE INVENTION

It is an object of the present invention to provide a new and improved method of eddy current scanning.

It is a further object of the present invention to provide a new and improved eddy current scanner which reduces the effects of surface irregularities contained in the surface scanned.

It is a further object of the present invention to provide a new and improved eddy current scanner for examining flaws located near surface irregularities.

It is a further object of the present invention to provide a new and improved eddy current scanner for examining fillets in gas turbine engine rotors.

SUMMARY OF THE INVENTION

In one form of the present invention, an eddy current probe is rotated along an arc about an axis for scanning an object. The probe is supported in a predetermined position with respect to the axis and is rotated about the axis at a constant speed.

BRIEF DESCRIPTION OF THE DRAWINGS

FIG. 1 illustrates one form of the present invention.

FIGS. 2A-C illustrate a pulley system contained in the embodiment of FIG. 1.

FIG. 3 illustrates schematically the operation of the pulley system of FIGS. 2A-C.

FIGS. 4A-C illustrate the scanning of an eddy current probe across a protrusion.

DETAILED DESCRIPTION OF THE INVENTION

FIG. 1 illustrates part of a gas turbine engine rotor 2 which contains dovetail slots 4A-B into which turbine blades (not shown) are inserted. The rotor 2 also contains bosses 7A-D. The bosses 7A-D contain bolt holes 10A-D which receive bolts for the purpose of mounting other engine components onto the rotor 2. The bosses 7A-D have flat top surfaces 12 and have curved fillets 11A-D in the regions where the bosses 7A-D attach to the rotor 2.

One form of the present invention is shown as an apparatus 15 positioned atop boss 7C. A support 18 contains a cylindrical pin 21 for insertion into the bolt hole 10C. Insertion of the pin 21 positions the support 18 against the top surface 12. The pin 21 is locked in the hole 10C by the action a cam lever 24 attached to the top of the pin 21 and a conical cam 27 attached to the bottom. The lever 24 pulls the pin 21 upward to draw the cam 27 against the walls of the hole 10C to prevent rotation of the pin 21 by locking the pin 21 in the hole 10C. The pin 21 provides a shaft about which the apparatus 15 can rotate in a manner later described. Thus, an axis of rotation 31 is provided by the pin and this axis 31 is preferably the pin's central axis in the case where pin 21 is cylindrical.

Affixed to the support 18 is an arm 33 supporting a bracket 35. The arm 33 is movable in the directions of arrows 36 by rotation of a knob 34 which is connected to the arm 33 by a threaded rod (not shown). The arm 33 can be locked in a selected position by means not shown. That is, the arm 33 and the bracket 35 are movable in the radial directions 36 with respect to the pin 21.

The bracket 35 contains an arcuate surface 38 containing an arcuate slot 41 which supports a hollow cylinder 44 which slides along the arcuate slot 41 in the directions of arrows 47. The cylinder 44 is constrained to remain perpendicular to the arcuate surface 38. A knurled nut 45A cooperates with a washer 45B to squeeze the washer 45B against a T-nut (not shown) on which the knurled nut 45A is threaded. This squeezing clasps the edges of the arcuate slot 41 between the washer 45B and the T-nut to thereby lock the cylinder 44 of a selected position along the arcuate slot 41. Thus, the cylinder 44 can be positioned at a predetermined angle 53 with respect to the axis of rotation 31.

A micrometer advance mechanism 54 known in the art is fastened to the end of the cylinder 44 and it advances a plunger 55 along the cylinder 44. An eddy current probe 56 fits within the hollow cylinder 44 in contact with the plunger 55 and the probe's axis 63 is preferably coincident with the central axis (not separately shown) of the cylinder 44. The probe 56 contains a coil 56A (not shown in FIG. 1, but in FIG. 4A) located near its tip 121 which radiates an electromagnetic field into the surface of the boss 7C. The field propagates in a direction generally along the axis 63 and perpendicular to the curved fillet 11C.

The probe 56 is movable along its axis 63 in the directions shown by arrows 61. The probe 56 can be locked in the cylinder 44 at a preselected position along the axis 63 by the micrometer advance mechanism 54 shown so that, once a particular angle 53 has been selected, a particular distance between the probe 56 and the fillet 11C can be selected. In being movable along the axis 63, the probe 56 has a component of motion along the axis of rotation 31. The component is a function of the cosine of the angle 53. Thus, the probe 56 can be said to be positionable at a predetermined angle with respect to, at a predetermined position along, and at a predetermined distance from, the axis of rotation 31.

A first sprocket 68 is affixed to the pin 21 and since the pin 21 is locked in the hole 10C, the first sprocket 68 is also fixed against rotation.

A second sprocket 71, which is driven by a motor 73, drives a drive chain 76 which is linked to the first sprocket 68 and to a third sprocket 79. The third sprocket 79 drives a potentiometer 81 through a shaft 82. The potentiometer 81 is fastened to the apparatus 15, thus allowing a rotational shaft angle 83 to be defined between the shaft 82 and the potentiometer 81. The significance of this shaft angle 83 will shortly become apparent. The functioning of the three sprockets is more clearly shown in FIGS. 2A–C, which are schematic top views of these sprockets.

In FIG. 2A, the sprockets 68, 71, and 79 are indicated as circles and the chain 76 as a belt. For geometric simplicity, the quarter circumferences 86 equal distances 89. A reference mark 91 is shown on the chain 76. Reference arrows 92A–C are shown on the three sprockets. Symbol 94 indicates that the first sprocket 68 does not rotate. Axes 99A–C connect the centers of the sprockets. These axes 99A–C form a triangle which is in constant angular relation with the apparatus 15.

As the motor-driven second sprocket 71 rotates as shown by arrow 101, the chain 76 pulls the second and third sprockets 71 and 79 around the first sprocket 68 so that the second and third sprockets travel in a circular path 103 and occupy the successive positions shown in FIGS. 2A–C. That is, the apparatus 15 rotates as shown by arrows 102 in FIG. 1. If the first and third sprockets in FIGS. 2A–C are of the same diameter, then angle 104 equals angle 106 during all stages of rotation. Since angle 104 is also the rotational shaft angle 83 of the potentiometer in FIG. 1, and since the angle 104 indicates the relative position of the assembly 15 with respect to the first sprocket 68, the equality of the two angles 104 and 106 allows the angular position of the assembly 15 with respect to the boss 7C in FIG. 1 to be deduced from the output of the potentiometer 81. This is further explained with reference to FIG. 3.

In FIG. 3, the potentiometer 81, which has a tap 107 (corresponding in position to arrow 92B in FIG. 2A) which rotates within a curved resistor 109 and which is powered by dc power supply 110, is shown superimposed upon the three sprockets 68, 71, and 79. A geometric analysis will show that, since the first sprocket 68 does not rotate, the tap 107 has the same angular relation shown by angle 104, with respect to the axis 99A as does the reference arrow 92A of the first sprocket 68 in FIG. 2A. That is, angle 104A equals angle 106 during rotation. As angle 104A changes during rotation, the output voltage $V_p$ of the potentiometer changes and this voltage $V_p$ is indicative of both angles 104A and 106. Thus, the output of the potentiometer 81 is indicative of the rotational position of the apparatus 15 in FIG. 1 with respect to the locked pin 21 and thus with respect to the boss 7C.

$V_p$ is compared by comparators 107A and 109A in FIG. 3 with two preselected voltages V1 and V2 which are tapped from variable resistors 112 and 115. The outputs of the comparators 107A and 109A are connected to circuits indicated as blocks 119 and 121. The circuits within these blocks 119 and 121 respond to the comparators 107A and 109A by reversing the motor 73 in FIG. 1 whenever the changing voltage $V_p$ in FIG. 3 reaches either of the voltages V1 or V2. Thus, V1 and V2 establish limits between which the potentiometer 81 voltage $V_p$ is constrained. This limits the rotation of the motor 73 in FIG. 1 between angular positions corresponding to these voltages. The voltages V1 and V2 thus define the length and rotational position of an arc along which the probe scans the boss 7C. Accordingly, a windshield-wiper-like scanning of the eddy current probe 56 in FIG. 1 is obtained between the two limits established by the variable resistors 112 and 115 in FIG. 3.

The motor 73 in FIG. 1 preferably scans the eddy current probe 56 at a constant speed, because it is knownd that this facilitates analysis of the signals produced by the eddy current probe 56. Prior to scanning, however, the eddy current probe 56 is positioned so that the tip 121 of the probe 56 is positioned approximately two thousandths of an inch above the surface scanned. The importance of this positioning will now be discussed.

As shown in FIG. 4A, an eddy current probe 56 is scanning a surface 123 and approaching a protrusion or irregularity 127, which may be a welding seam or a mold parting line resulting from electrochemical machining. The electromagnetic energy radiated by the probe 56 is illustrated by the dotted lobe 130, which is a highly schematic polar plot of the radiated energy distribution. As is well known, the probe 56 responds to changes in the electromagnetic characteristics of the material present within the lobe 130.

When the probe 56 reaches the irregularity 127, if the probe 56 follows the contour of the irregularity 127 (that is, if the probe 56 is moved in the direction of arrow 133), then the electromagnetic characteristics of the materials contained within the lobe 130 drastically change. That is, prior to reaching the irregularity 127, the regions 134A of the lobe 130 in FIG. 4A are occupied by the surface of the material 123. Upon reaching the irregularity 127, the regions 134A of the lobe 130 become occupied by the ambient dielectric medium (e.g., air) as shown in FIG. 4B. Thus, while not necessarily exactly shown to scale by FIG. 4B, the percentage change of the ambient dielectric medium in the lobe 130 upon reaching the irregularity 127 is relatively great (as compared with the change about to be discussed) and thus the change in inductance of the probe 56 due to the surface irregularity 127 is similarly great.

However, if the probe 56 is positioned at a selected distance (dimension 128), such as two thousandths of an inch, away from the surface 123 during scanning as shown in FIG. 4C (i.e., the probe 56 has a standoff of 0.002"), the change in inductance because of the irregularity 127 is reduced. One explanation for this is that the proportional change in the amount of ambient dielectric medium (namely, that amount in the shaded region 135) which is displaced by the irregularity 127 is a relatively small fraction of the total dielectric medium within the lobe 130. That is, the change in dielectric medium indicated as shaded region 138 in FIG. 4B is greater than the change indicated as shaded region 135 in FIG. 4C. Thus, the influence of the irregularity 127 upon the inductance of the eddy current probe 56 is reduced. Accordingly, the existence of a surface irregularity 127 does not so greatly mask an inductance signal produced by a flaw such as 140 in FIG. 4C which is located beneath the surface irregularity 127. Therefore, the effects of surface irregularities upon the signal produced by the eddy current probe 56 have been reduced.

The probe 56 is shown in FIG. 4B as being in contact with the irregularity 127. However, as mentioned in the Background of the Invention, the probe can be accidentally bounced away from the surface of the material 123 by impact with the irregularity 127 or intentionally raised to hurdle the irregularity 127. In such cases, the probe 56 will probably not be in contact with the irregularity 127 as shown in FIG. 4B, but will be positioned at a distance from the irregularity 127.

Similarly, the positioning of the probe 56 at a predetermined standoff of two thousandths of an inch will probably not result in contact between the probe 56 and the irregularity 127 as shown in FIG. 4C. FIG. 4C shows contact for diagrammatic simplicity. Of course, the predetermined distance 128 is not maintained in the vicinity of the irregularity 127 as shown in FIG. 4C: the distance 128 becomes reduced. Accordingly, the predetermined distance 128 is not strictly the distance between the probe 56 and the surface 123, but is the distance such as distance 129 between the probe and a predetermined reference such as dashed line 129A. The distance 129 does not change in the vicinity of irregularity 127.

Further, it has been found that a signal produced by a crack 145 located within, or on the surface of, the irregularity 127 is itself masked less by scanning with probe 56 using standoff than without. It is believed that one reason for this lies in the fact that, while the probe inductance is changed as described in connection with FIGS. 4A–C, the material in the irregularity 127 still offers a somewhat continuous eddy current path. However, the existence of crack 145 serves to break the continuity and to produce eddy current signals.

An invention has been described wherein an eddy current probe 56 can be positioned in a predetermined manner with respect to a first reference, namely, the axis of rotation 31 in FIG. 1. This is accomplished by the combined positioning of the probe along the axis 63, by adjusting the angle 53, and by the adjustment of the probe 56 in the radial direction along arrows 36. A motor 73 rotates the probe 56 about the axis of rotation 31 between selected limits to scan the probe 56 along the surface of an object in windshield-wiper fashion. The invention allows the probe 56 to be raised above the surface a selected distance during scanning in order to hurdle surface irregularities. That is, a stand-off feature is provided to reduce the masking effect that surface irregularities have upon flaws. In the description above, it has been tactily assumed that the axis 63 is coplanar with the axis of rotation 31. However, this is not necessary and different relations between the probe axis 63 and the axis of rotation 31 may be used in different situations.

Viewed another way, the apparatus 15 is journaled about the locked pin 21 which provides an anchor used by the apparatus 15 to swing the eddy current probe 56 along an arc which follows the surface of the boss 7C. The probe 56 can be advanced and retracted from the boss 7C in selected distances. A rotation means is provided by the motor 73. A control means, which includes the circuitry producing the voltages V1 and V2, controls the motor 73 so that the probe 56 swings along a predetermined arc whose position and length are determined by the voltages V1 and V2.

Numerous modifications and substitutions can be made without departing from the true spirit and scope of the present invention.

What is desired to be secured by Letters Patent of the United States is the following.

I claim:

1. Apparatus for scanning the surface of a bolt hole boss in a gas turbine engine rotor, using an eddy current probe, comprising:
    (a) support means fastened to, and rotatable about, the boss for carrying the eddy current probe along a predetermined arc, having
        (i) a pin for insertion into the bolt hole for providing a center of rotation of the support,
        (ii) a bracket
            (A) for positioning the eddy current probe generally coplanar with the pin and at a selectable angle with respect to the pin and
            (B) including means for advancing the eddy current probe into contact with the surface of the boss and then retracting the probe a predetermined distance from the surface, and
        (iii) an arm for positioning the bracket of (a)(ii) at a selectable distance from the pin,
    (b) motive means for rotating the support means of (a) at a substantially constant speed about the center of rotation of (a)(i), and
    (c) limiting means for establishing the length of the arc of (a).

2. Apparatus according to claim 1 in which the limiting means of (c) comprises:
    (d) means for producing a position signal indicative of the relative rotational position between the eddy current probe and the boss,
    (e) means for establishing two limit signals indicative of two selected points on the arc of (a), and
    (f) means for
        (i) receiving the position signal and the limit signals and
        (ii) limiting the travel of the probe along the arc so that the position signal remains within bounds determined by the limit signals.

* * * * *